United States Patent
Matelich (10) Patent No.: US 9,267,104 B2
(45) Date of Patent: *Feb. 23, 2016

(54) NOX REMOVAL SYSTEM FOR BIOGAS ENGINES AT ANAEROBIC DIGESTION FACILITIES

(75) Inventor: Michael Matelich, San Diego, CA (US)

(73) Assignee: BIOGAS & ELECTRIC, LLC, San Diego, CA (US)

( * ) Notice: Subject to any disclaimer, the term of this patent is extended or adjusted under 35 U.S.C. 154(b) by 505 days.

This patent is subject to a terminal disclaimer.

(21) Appl. No.: 13/519,539

(22) PCT Filed: Dec. 22, 2010

(86) PCT No.: PCT/US2010/061780
§ 371 (c)(1),
(2), (4) Date: Jun. 27, 2012

(87) PCT Pub. No.: WO2011/082060
PCT Pub. Date: Jul. 7, 2011

(65) Prior Publication Data
US 2012/0311997 A1 Dec. 13, 2012

Related U.S. Application Data

(63) Continuation-in-part of application No. 12/882,901, filed on Sep. 15, 2010, now Pat. No. 8,012,746.

(60) Provisional application No. 61/335,072, filed on Dec. 31, 2009.

(51) Int. Cl.
*C12M 1/107* (2006.01)
*C12M 1/00* (2006.01)
(Continued)

(52) U.S. Cl.
CPC ............... *C12M 43/08* (2013.01); *C12M 21/04* (2013.01); *B01D 53/56* (2013.01); *B01D 53/60* (2013.01); *B01D 53/84* (2013.01); *C12M 21/02* (2013.01); *Y02E 50/343* (2013.01)

(58) Field of Classification Search
CPC ...... C12M 21/02; C12M 21/04; C12M 43/08; B01D 53/56; B01D 53/60; B01D 53/84; B01D 53/85
USPC ..................... 435/266, 292.1, 300.1; 210/603
See application file for complete search history.

(56) References Cited

U.S. PATENT DOCUMENTS 3,881,004 A 4/1975 Kelly et al.
3,989,797 A 11/1976 Brady et al.
(Continued)

FOREIGN PATENT DOCUMENTS

CN 1155521 7/1997
DE 3840517 A1 6/1990
(Continued)

OTHER PUBLICATIONS

Andrae and Bjornbom, "Design concept to reduce fuel NOx in catalytic combustion of gasified biomass," AIChE Journal 49: 2149-2156 (2003).
(Continued)

*Primary Examiner* — William H Beisner
(74) *Attorney, Agent, or Firm* — Wilson Sonsini Goodrich & Rosati (57) ABSTRACT

Provided herein are methods, devices and systems comprising a reactor that is operatively connected to: (a) a biogas production unit for converting waste to a biogas stream; and (b) an engine that utilizes the biogas stream from the biogas producing unit to produce energy and an engine exhaust.

15 Claims, 5 Drawing Sheets

(51) Int. Cl.
B01D 53/60 (2006.01)
B01D 53/56 (2006.01)
B01D 53/84 (2006.01)

(56) References Cited

U.S. PATENT DOCUMENTS

| | | | |
|---|---|---|---|
| 4,201,752 A | | 5/1980 | Kosseim |
| 4,723,968 A | * | 2/1988 | Schippert et al. ............... 95/205 |
| 4,825,843 A | | 5/1989 | Novy |
| 5,279,963 A | | 1/1994 | Hobby |
| 5,465,690 A | | 11/1995 | Viel Lamare et al. |
| 5,518,696 A | | 5/1996 | Jain |
| 5,581,998 A | | 12/1996 | Craig |
| 5,702,572 A | | 12/1997 | Fujimura et al. |
| 5,817,282 A | | 10/1998 | Radlein et al. |
| 5,876,662 A | | 3/1999 | Jain |
| 6,013,512 A | * | 1/2000 | Turschmid et al. ........... 435/266 |
| 6,062,092 A | | 5/2000 | Weaver |
| 6,174,498 B1 | | 1/2001 | Jain et al. |
| 6,393,821 B1 | | 5/2002 | Prabhu |
| 6,548,197 B1 | | 4/2003 | Chandran et al. |
| 6,602,092 B2 | | 8/2003 | Soubh |
| 6,923,004 B2 | | 8/2005 | Chandran et al. |
| 6,948,436 B2 | | 9/2005 | Mooney et al. |
| 7,014,682 B2 | | 3/2006 | Hickerson et al. |
| 7,059,205 B1 | | 6/2006 | Weaver |
| 7,272,934 B2 | | 9/2007 | Chandran et al. |
| 7,276,366 B2 | | 10/2007 | Parker et al. |
| 7,387,719 B2 | | 6/2008 | Carson et al. |
| 7,426,891 B2 | | 9/2008 | Loving |
| 7,514,053 B2 | | 4/2009 | Johnson et al. |
| 7,585,359 B2 | | 9/2009 | Withiam et al. |
| 7,614,215 B2 | | 11/2009 | Warner et al. |
| 7,641,874 B2 | | 1/2010 | Cha |
| 7,644,579 B2 | | 1/2010 | Roberts et al. |
| 7,685,737 B2 | | 3/2010 | Gorbell et al. |
| 8,012,746 B2 | | 9/2011 | Matelich |
| 2003/0008381 A1 | | 1/2003 | Augenstein |
| 2003/0083391 A1 | | 5/2003 | Jahnke et al. |
| 2003/0110994 A1 | | 6/2003 | Lissianski et al. |
| 2004/0238654 A1 | | 12/2004 | Hagen et al. |
| 2005/0064577 A1 | * | 3/2005 | Berzin .......................... 435/266 |
| 2006/0070587 A1 | | 4/2006 | Bhalsora et al. |
| 2006/0129020 A1 | | 6/2006 | Barends |
| 2008/0009055 A1 | * | 1/2008 | Lewnard ....................... 435/262 |
| 2008/0050800 A1 | | 2/2008 | McKeeman et al. |
| 2008/0173176 A1 | | 7/2008 | Duesel et al. |
| 2008/0179177 A1 | | 7/2008 | Cha |
| 2010/0143209 A1 | | 6/2010 | Cha |
| 2011/0065166 A1 | | 3/2011 | Matelich |
| 2015/0024452 A1 | | 1/2015 | Matelich |

FOREIGN PATENT DOCUMENTS

| | | |
|---|---|---|
| DE | 4041820 | 6/1992 |
| DE | 4331932 A1 | 3/1994 |
| DE | 102007007510 A1 | 4/2008 |
| KR | 10-0794208 | 1/2008 |
| WO | WO-2011/082060 | 7/2011 |

OTHER PUBLICATIONS

Brogan et al., "Absorption of NO in an aqueous solution of NaClO2," Chem Eng Technol 21: 61-70 (1998).
Burke, Dairy waste anaerobic digestion handbook, Jun. 2001, pp. 1-54.
Busc and Pistarino, "Abatement of ammonia and amines from waste gases: a summary," J Loss Prev Process Industries 16: 157-163 (2003).
Dhar et al., "Photo-oxidation of nitrite to nitrate," Nature, Feb. 10, 1934 pp. 213-214.
EPA-450/1-78-001, Control Techniques for Nitrogen Oxides Emissions from Stationary Sources—Second Edition, Jan. 1978, 390 pages.
EPA-450/3-91-026, Alternative Control Techniques Document—Nitric and Adipic Acid Manufacturing Plants, Dec. 1991, 126 pages.
EPA-450/3-91-026, Alternative Control Techniques Document—Nitric and Adipic Acid Manufacturing Plants, Dec. 1991, 147 pages.
First and Viles, "Cleaning of stack gases containing high concentrations of nitrogen oxides," J. Air Pollution Control Assoc. 21: 122-127 (1971).
Fulks et al., "A review of solid materials as alternative ammonia sources for lean NOx reduction with SCR," SAE International Brochure 2009.
Kirk-Othmer, "Nitric acid," Encyclopedia of Chemical Technology vol. 17, pp. 1-27 1982.
Knol et al., "Reduction of nitrogen oxides by injection of urea in the freeboard of a pilot scale fluidized bed combustor," Fuel 68: 1565-1569 (1989).
Krase and Hetherington, "Removal of carbon dioxide from gas mixtures intended for ammonia synthesis," Ind Eng Chem 19: 208-211 (1927).
Lund, Pollution Control in the Chemical Industry from HF Lund Industrial Pollution Control Handbook, pp. 14-9 to 14-11 McGraw-Hill 1971.
Lund, Source Control—Chemical Control of Nitrogen Oxides from HF Lund Handbook of Air Pollution Control Technology, pp. 654-656 McGraw-Hill 1971.
McCandless et al., "Reduction of nitric oxide with metal sulfides," Ind Eng Chem Process Des Dev 19: 108-113 (1980).
PCT/US2010/061780 International Preliminary Report on Patentability, Jul. 4, 2012.
PCT/US2010/061780 International Search Report dated Aug. 24, 2011.
Rossi, "How to Control NOx," Pollution Engineering Apr. 1995 pp. 50-52.
Smith, "NOx emission control demands a range of solutions," Power Engineering 96 (7):44(4) (1992).
SMUD Digester Engine Project, ICAT 2008, "Removal of H2S from biogas and NOx from engine exhaust at a dairy digester using microwave technology," updated Mar. 3, 2009, printed out on Aug. 4, 2009 http://www.arb.ca.gov/research/icat/projects/08smud.htm.
Streichsbier and Dibble, "Non-catalytic NOx removal from gas turbine exhaust with cyanuric acid in a recirculating reactor," Thesis: University of California, Berkeley 1998, http://www.biofuels.coop/archive/nox_reducer.pdf.
Tseng et al., "The effect of in-situ ammonium—sulphur aerosols on the removal of SO2, NOx and mercury from combustion flue gas," The Conference on Selective Catalytic and Non-Catalytic Reduction for NOx control, Pittsburgh PA May 17-18 2000.
CA2785368 Office Action dated Jul. 22, 2013.
CN201080064956.8 Office Action dated Apr. 23, 2014.
PCT/US2010/061780 International Preliminary Report on Patentability Jul. 12, 2012.
PCT/US2010/061780 International Search Report and Written Opinion dated Aug. 25, 2011.
U.S. Appl. No. 12/882,901 Office Action dated Feb. 3, 2011.
Ando et al. Nitrogen Oxides Abatement Technology in Japan—1973, Environmental Tech. Ser., EPA-R-2-73-284, U.S. EPA Research Triangle Park, pp. 21-22, Jun. 1973.
Ando et al. NOx Abatement for Stationary Sources, EPA-600/2-76-013B. Jan. 1976.
BASF Catalog: http://www.catalysts.basf.com/p02/USWeb-Internet/catalysts/en/content/microsites/catalysts/prods-inds/stationary-emissions/scr-cat-pow-gen Accessed Oct. 8, 2014.
Battelle. Environmental Technology Verification Report. Mar. 2003.
CleanAir, Portable Flue Gas Analyzer, http://express.cleanair.com/PortableGasAnalyzers/testo.html?gclid=CM2GqvDKtLgCFa9_QgodEFoAzA accessed Oct. 8, 2014.
Johnson Matthey Catalog: http://jmcct.com/products-services?f%5bc%5d=heterogeneous-catalysts Accessed Oct. 8, 2014.
Johnson. Diesel Emission Control in Review. SAE In. J. Fuels Lubr. 2(1):1-12 (2009).

(56) References Cited

OTHER PUBLICATIONS

Landong et al. Catalytic Oxidation of NO Over $TiO_2$ Supported Platinum Clusters I. Preparation, Characterization and Catalytic Properties. Applied Catalysis B: Environmental (2010), 93(3-4):259-266.

Lund. Pollution Control in the Chemical Industry; from H.F. Lund Handbook of Air Pollution Control Technology. p. 14-11, McGraw-Hill 1971.

Lund. Source Control-Chemical: Control of Nitrogen Oxides, from H.F. Lund; Handbook of Air Pollution Control Technology. p. 656, McGraw-Hill 1971.

Matelich et al. NOxRx: A wet-scrubbing solution for NOx and SOx emissions from stationary biogas engines. A White Paper, published online Jul. 22, 2013.

Opportunities for Combined Heat and Power at Wastewater Treatment Facilities: Market Analysis and Lessons from the Field. http://www.epa.gov/chp/documents/wwtf_opportunities.pdf Oct. 2011.

PCT/US2014/046902 International Search Report and Written Opinion dated Nov. 7, 2014.

Rittsteig et al. Anaerobic Treatment of a Concentrated Urea Wastewater with Simultaneous Stripping of Ammonia. Appl. Microbiol. and Biotechnol. (2001), 56(5-6):820-825.

Roy et al. NOx Storage-Reduction Catalysis: From Mechanism and Materials Properties to Storage-Reduction Performance. Chem. Rev. (Sep. 2009); 109(9):4054-91.

Shiba et al. Catalytic Oxidation of no to NO Over Cr/TiO and Cu/TiO under Oxidizing Atmosphere. (1996), 58(1):133-137.

Skalaska Trends in NOx Abatement: A Review. Science of the Total Environment (2010) 408(19):3976-3989.

Sud-Chemie Catalog: http://www.power-technology.com/contractors/environmental/sud-chemie/ Accessed Oct. 8, 2014.

Twigg. Catalytic Control of Emissions from Cars. Catalysis Today (2011), 163(1):33-41.

Twigg. Controlling Automotive Exhaust Emissions: Successes and Underlying Science. Philos. Trans. A. Math Phys. Eng. Sci. (Apr. 15, 2005);363(1829):1013-33.

Wenzhi Lu et al. Catalytic Oxidation of NO. Chinese Journal of Catalysis. vol. 21, No. 5, Sep. 2000.

U.S. Appl. No. 14/333,429 Office Action dated Nov. 6, 2015.

\* cited by examiner

NOX REMOVAL SYSTEM FOR BIOGAS ENGINES AT ANAEROBIC DIGESTION FACILITIES

CROSS REFERENCE

This application is filed pursuant to 35 U.S.C. §371 as a United States National Phase Application of International Application Ser. No. PCT/US10/061780, filed Dec. 22, 2010, which claims priority to and the benefit of U.S. application Ser. No. 12/882,901 filed Sep. 15, 2010 (now U.S. Pat. No. 8,012,746) and U.S. Appl. Ser. No. 61/335,072 filed Dec. 31, 2009, each of which are incorporated herein by reference in their entirety.

BACKGROUND OF THE INVENTION

The United States Environmental Protection Agency (EPA)'s mission is to protect human health and the environment. To achieve this mission, EPA implements a variety of programs under the Clean Air Act that focus on reducing outdoor, or ambient, concentrations of air pollutants that cause smog, haze, acid rain, and other problems; reducing emissions of toxic air pollutants that are known to, or are suspected of, causing cancer or other serious health effects; and phasing out production and use of technologies that destroy stratospheric ozone. These pollutants come from stationary sources (such as chemical plants, gas stations, and power plants) and mobile sources (such as cars, trucks, and planes). State and local governments have also enacted legislation and implemented guidelines to encourage the development of clean technologies.

SUMMARY OF THE INVENTION

Biogas engines pollute the environment by contaminating air with NOx emissions. Accordingly, local, state and federal NOx regulations have established maximum levels of NOx production for biogas engines. For example, the California Energy Commission (CEC) has established guidelines for certification of combined heat and power engine systems, including for example, biogas engines, that limit NOx emission levels pursuant to California's recently enacted Waste, Heat and Carbon Emissions Reduction Act. Similarly, the local San Joaquin Air Board has established Rule 4702 that governs NOx emissions of biogas engines. These stringent NOx emission standards are a hindrance to the operation of biogas engines.

NOx, however, is not the only greenhouse gas. California, as an example, is home to about 1,750 dairies and 1.8 million dairy cows, producing in aggregate about 35-40 million tons of manure each year. Manure management consists primarily of converting the raw manure to a form that is acceptable for spreading on agricultural fields. Typically, flush water from animal holding areas is transferred to settling tanks for removal of large solid particles, and then stored in holding ponds. During the holding period, anaerobic bacteria convert carbohydrates, fatty acids, and other high energy organic compounds to methane and carbon dioxide that is then typically released into the atmosphere. The liquid suspension remaining after this stabilization process has reduced odor, reduced pathogens, and is less attractive to flies and other nuisance species. As a result of these processes, large quantities of the greenhouse gas methane are released into the atmosphere. Methane is approximately 21 times more potent than carbon dioxide in its global warming potential, and its relatively short atmospheric half life of 12 years makes it an excellent candidate for reducing global warming in the short term. Biogas produced by anaerobic digestion of dairy manure is 50-65% methane, with the remainder being carbon dioxide and a variety of trace gases including hydrogen sulfide. Collecting and combusting the biogas mixture in a reciprocating internal combustion engine has a two-fold favorable effect on greenhouse emissions. The methane is converted to an equal quantity of carbon dioxide, a gas with lower greenhouse warming potential, and the production of an approximately equal quantity of carbon dioxide from the burning of fossil fuels is avoided. The methane produced and released into the atmosphere by California dairy manure management processes totals 450,000 tons per year. It is envisioned by the instant inventors that utilizing methane from dairy farms for electricity generation would be equivalent to removing 2 million motor vehicles from operation. There is currently an estimated 1,000 dairies in California alone that will benefit from the technology described herein.

NOx emissions from combustion of biogas generated by anaerobic digestion facilities are a serious problem that significantly impedes expansion of biogas utilization for electricity generation. Nitrogen oxides are one of six criteria pollutants for which the Clean Air Act requires the EPA to set National Ambient Air Quality Standards (NAAQS). While exposure to high levels of nitrogen oxides has human health effects, their adverse environmental effects are primarily due to secondary reactions in the atmosphere. For example, the photochemical reaction of $NO_2$ with volatile organic compounds (VOC's) produces ozone, an important air pollutant and lung irritant. Under the Clean Air Act, each state must develop a plan describing how it will meet the NAAQS. Most of the state of California, including the San Joaquin Valley that serves as home to most of the state's dairy farms, fall within a NAAQS ozone non-attainment zone. Distributed generation projects in non-attainment zones are considered "minor sources" subject to emissions standards set by the states. For all new distributed generation facilities coming on line after Jan. 1, 2007, the California Air Resource Board (CARB) has set NOx emissions limits of 0.07 lb/MW hr. The current high cost of reducing NOx emissions has effectively suspended many California manure based anaerobic digestion projects. The fraction of U.S. counties lying within ozone non-attainment zones is expected to increase over coming years as increasingly strict NAAQS come into effect. In fact, it is believed by many in the industry that without an expensive transition metal-based catalytic convertor, the exhaust from the biogas engine contains levels of NOx too high to legally operate.

Internal combustion engines using biogas (or other fuels) produce a mixture of nitrogen oxides including nitric oxide (NO) and nitrogen dioxide ($NO_2$) and other NOx gases via oxidation of atmospheric nitrogen. Conventional reciprocating engines operating without exhaust gas treatment modalities produce approximately 1.4 pounds of NOx per megawatt hour (MWh) which is 20 times the current CARB standard. The benefits to the water and air quality provided by the subject matter described herein are significant.

Provided herein are methods, devices, and systems for the attenuation of NOx emission from biogas combustion utilizing a liquid waste stream and application of principles of extended absorption, wet chemical scrubbing, and/or selective non-catalytic reduction.

In a first aspect, described herein are methods, devices, and systems comprising a reactor that is operatively connected to: (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit.

In a second aspect, provided herein are methods, devices, and systems comprising an engine exhaust that is operatively connected to a reactor and exhaust from the reactor contains an amount equal to or less than about 0.4 grams of NOx per horsepower-hour of energy produced by the engine.

In a third aspect, provided herein are methods, devices, and systems comprising an engine exhaust that is operatively connected to a reactor and exhaust from the reactor contains an amount equal to or less than about 1 pound of NOx per MWh of energy produced by the engine.

In a fourth aspect, described herein are methods, devices, and systems comprising a biogas production unit for converting waste to a biogas stream and an engine that is operatively connected to a reactor and the operable connection between the engine and the reactor contains an injection inlet for the introduction of a reactive chemical agent to contact the engine exhaust prior to entrance of the engine exhaust into the reactor.

In a fifth aspect, provided herein is a reactor that is operatively connected to: (a) a biogas production unit for converting waste to a biogas stream; and (b) an engine that utilizes the biogas stream from the biogas producing unit to produce energy and an engine exhaust; wherein the engine exhaust is operatively connected to the reactor and exhaust from the reactor contains an amount equal to or less than about 0.4 grams of NOx per horsepower-hour of energy produced by the engine.

In a sixth aspect, provided herein is a reactor that is operatively connected to: (a) a biogas production unit for converting waste to a biogas stream; and (b) an engine that utilizes the biogas stream from the biogas producing unit to produce energy and an engine exhaust; wherein the engine exhaust is operatively connected to the reactor and exhaust from the reactor contains an amount equal to or less than about 1 pound of NOx per MWh of energy produced by the engine.

In a seventh aspect, provided herein is a method comprising the step of decreasing NOx emissions in a reactor that is operatively connected to (a) a biogas production unit for converting waste to a biogas stream; and (b) an engine that utilizes the biogas stream from the biogas producing unit to produce energy and an engine exhaust; wherein the engine exhaust is operatively connected to the reactor and the operable connection between the engine exhaust and the reactor contains an injection inlet for the introduction of a reactive chemical agent to contact the engine exhaust prior to entrance of the engine exhaust into the reactor.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a reactor filled with packing media to increase the surface area.

DETAILED DESCRIPTION

The embodiments of the subject matter provided herein provide diaries, biogas engine providers, anaerobic digester facilities, and other producers and contributors of harmful gases to the environment with technology to make efforts to meet or exceed air quality regulations. An advantage of the subject matter provided herein is the use of spent liquid waste from the on-site anaerobic digester to scrub NOx from an engine or cogeneration unit's exhaust stream in an inexpensive manner. Liquid and/or vapor NOx extraction and subsequent chemical conversion processes is enhanced by the unique liquid/vapor continuous-flow design of the subject matter provided herein which ensures a large excess of chemical reductant and limited contact time to enhance NOx removal while minimizing unwanted reverse reaction due to by-product saturation.

A feature of the subject matter provided herein is a reactor that is operatively connected to: (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit. As used herein, "biogas stream" comprises at least 50% methane. As used herein, "NOx" means oxides of nitrogen including as non-limiting examples NO, $NO_2$, and $N_2O_5$. As used herein, "COx" means oxides of carbon. As used herein, "SOx" means oxides of sulfur, including as one non-limiting example $SO_2$.

In certain embodiments, a reactor decreases SOx, NOx, and/or COx emissions from engine exhaust by contacting the engine exhaust with a liquid waste stream.

In further or additional embodiments, provided is a biogas production unit for converting waste to a biogas stream is an anaerobic digester. In some embodiments, provided is an anaerobic digester wherein the waste is agricultural waste. In some embodiments, the agricultural waste comprises feces or urine. In further or additional embodiments, the waste is municipal waste. In still further embodiments, the municipal waste comprises wastewater. In some embodiments, described herein is a system wherein the biogas production unit is a landfill. In further or additional embodiments, a waste stream is piped into a reactor from or at a landfill.

Biogas Production Unit

Another feature of the subject matter provided herein is a biogas production unit that is adapted to produce energy and an engine exhaust, and is operatively connected to a reactor that decreases NOx emissions from the engine exhaust by contacting the engine exhaust with a liquid waste stream provided from the biogas production unit. For example, in certain embodiments, the biogas production unit is an anaerobic digester. Anaerobic digesters are commercially available from the following sources: Accent Manufacturing, Inc.; Advanced Green Energy Solutions LLC; Acterra Group, Inc.; ADI Systems Inc.; American Anaerobic Digestion; Andgar Corporation; Applied Technologies, Inc.; BioEnergy Solutions; BIOFerm Energy Systems; Biogas Energy Inc.; Bioprocess Control AB; Boerger LLC; CCl BioEnergy Inc.; CH Four Biogas, Inc.; EcoCorp; Ecovation, Inc.; Energies Direct LLC; Entec Biogas USA/Reynolds Inc.; Environmental Credit Corp. (ECC); Environmental Fabrics, Inc.; Environmental Power/Microgy; Environmental Products & Technologies Corporation; Firestone Specialty Products; Gen-Tec LLC; GHD, Inc.; Groth Corporation; Industrial Telemetry Inc.; Integrys Energy Services, Inc.; NewBio E Systems, Inc.; Onsite Power Systems; Organic Waste Systems nv (OWS); Patz Corporation; Phase 3 Renewables; RCM International; ROS ROCA Envirotec; Schmack BioEnergy; Vaughan Company, Inc.; WesTech Engineering, Inc.; and Williams Engineering Associates.

Waste from a Biogas Production Unit

An additional feature of the subject matter provided herein is a biogas production unit including but not limited to an anaerobic digester that is adapted to convert a waste to a biogas stream. In certain embodiments, the waste is agricultural waste. In further or additional embodiments, the agricultural waste comprises feces or urine. In some embodiments, the animal waste is manure. Most animal manure is feces. Common forms of animal manure include farmyard manure (FYM) or farm slurry (liquid manure). FYM also contains plant material (often straw), which has been used as bedding for animals and has absorbed the feces and urine. Agricultural manure in liquid form, known as slurry, is produced by more intensive livestock rearing systems where concrete or slats are used, instead of straw bedding. Manure from different animals may have different qualities and require different application rates, such as manure from farm animals such as horses, cattle, pigs or sheep, chicken and turkey manures, rabbit manure, human sewage and guano from seabirds and bats. For instance, sheep manure is high in nitrogen and potash, and pig manure is relatively low in both. Horse manure also contains lots of weed seeds, as horses do not digest seeds the way that cattle do. Chicken manure, even when well rotted, is very concentrated and should be used sparingly.

In some embodiments, the waste is municipal waste. Municipal waste results at least in part from anthropogenic effects, processes or materials that are derived at least in part from human activities. In certain embodiments, the municipal waste comprises wastewater. Wastewater comprises any water that has been adversely affected in quality by anthropogenic influence. In certain embodiments, wastewater comprises liquid waste discharged by domestic residences, commercial properties, industry, and/or agriculture and can encompass a wide range of potential contaminants and concentrations. In the most common usage, it refers to the municipal wastewater that contains a broad spectrum of contaminants resulting from the mixing of wastewaters from different sources. In further or additional embodiments, the waste is sewage. Sewage is a subset of wastewater that is contaminated with feces or urine. As used herein, "sewage" includes domestic, municipal, or industrial liquid waste products disposed of, usually via a pipe or sewer or similar structure including for example a cesspool emptier. In still further or additional embodiments, the waste comprises an organic material, including for example waste from food processing facilities, paper mills, meat processing facilities, and the like.

Waste from a Landfill

An additional feature of the subject matter provided herein is the use of biogas (including for example methane) from a landfill as fuel for an engine and further utilizing a liquid waste stream to reduce levels of NOx, SOx, and/or COx emissions from the engine. In some embodiments, the liquid waste stream is from an anaerobic digester. In further or additional embodiments, the landfill-produced biogas is piped into an engine, including for example an internal combustion engine. Thus, it is contemplated that the waste from a landfill (e.g., methane) is utilized to power an engine, and further liquid waste from an anaerobic digester is contacted with emissions from the engine to reduce the levels of NOx, SOx, and/or COx.

Levels of Emissions from Reactor

Another feature of the subject matter provided herein are systems, methods and devices that are compliant with local, state and federal regulations that have established maximum levels of NOx, SOx, and/or COx emission limitations on emissions for biogas engines. In some embodiments, the methods, devices and systems provided herein are compliant with the NOx emission levels required by the California Energy Commission (CEC) guidelines for certification of combined heat and power engine systems established pursuant to California's recently enacted Waste, Heat and Carbon Emissions Reduction Act as of Sep. 1, 2010. In further or additional embodiments, the methods and devices and systems provided herein provide a decrease in emission levels over the conventional methods, devices, and/or systems, but are not compliant with the California Energy Commission (CEC) guidelines for certification of combined heat and power engine systems established pursuant to California's recently enacted Waste, Heat and Carbon Emissions Reduction Act as of Sep. 1, 2010

Reduction in NOx Emissions

In some embodiments, provided herein are systems, methods and devices comprising a reactor that is operatively connected to (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit wherein the engine exhaust is operatively connected to the reactor and exhaust from the reactor contains an amount equal to or less than about 1 pound of NOx per MWh of electrical energy produced by the engine crediting mechanical energy produced at the rate of 1 MWh per 1,341 horsepower-hour (hp-hr).

In further or additional embodiments, provided herein are systems, methods and devices comprising a reactor that is operatively connected to (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit wherein exhaust from the reactor contains an amount equal to or less than about 0.9 pounds of NOx per MWh of electrical energy produced by the engine crediting mechanical energy produced at the rate of 1 MWh per 1,341 horsepower-hour (hp-hr), or exhaust from the reactor contains an amount equal to or less than about 0.75 pounds of NOx per MWh of energy produced by the engine crediting mechanical energy produced at the rate of 1 MWh per 1,341 horsepower-hour (hp-hr), or exhaust from the reactor contains an amount equal to or less than about 0.5 pounds of NOx per MWh of energy produced by the engine crediting mechanical energy produced at the rate of 1 MWh per 1,341 horsepower-hour (hp-hr), or exhaust from the reactor contains an amount equal to or less than about 0.4 pounds of NOx per MWh of energy produced by the engine crediting mechanical energy produced at the rate of 1 MWh per 1,341 horsepower-hour (hp-hr), or exhaust from the reactor contains an amount equal to or less than about 0.3 pounds of NOx per MWh of energy produced by the engine crediting mechanical energy produced at the rate of 1 MWh per 1,341 horsepower-hour (hp-hr), or exhaust from the reactor contains an amount equal to or less than about 0.2 pounds of NOx per MWh of energy produced by the engine crediting mechanical energy produced at the rate of 1 MWh per 1,341 horsepower-hour (hp-hr), or exhaust from the reactor contains an amount equal to or less than about 0.1 pounds of NOx per MWh of energy produced by the engine crediting mechanical energy produced at the rate of 1 MWh per 1,341 horsepower-hour (hp-hr), or exhaust from the reactor contains an amount equal to or less than about 0.07 pounds of NOx per MWh of energy produced by the engine crediting mechanical energy produced at the rate of 1 MWh per 1,341 horsepower-hour (hp-hr), or exhaust from the reactor contains an amount equal to or less than about 0.05 pounds of NOx per MWh of energy produced by the engine crediting mechanical energy produced at the rate of 1 MWh per 1,341 horsepower-hour (hp-hr), or exhaust from the reactor contains an amount equal to or less than about 0.03 pounds of NOx per MWh of energy produced by the engine crediting mechanical energy produced at the rate of 1 MWh per 1,341 horsepower-hour (hp-hr), or exhaust from the reactor contains an amount equal to or less than about 0.01 pounds of NOx per MWh of energy produced by the engine crediting mechanical energy produced at the rate of 1 MWh per 1,341 horsepower-hour (hp-hr).

In further or additional embodiments, the methods and devices and systems provided herein are compliant with the NOx emission levels of Rule 4702 of the San Joaquin Air Board established as of Sep. 1, 2010. The San Joaquin Air Board determines the NOx emission level by: (1) measuring NOx concentration in the exhaust; and (2) measuring the oxygen concentration in the exhaust. To correct for the differences in the oxygen level for two kinds of engines (rich v. lean burn engines), the Board adjusts proportionately both the NOx and the oxygen concentration so that the oxygen level in the exhaust equals 15%. For example, if the exhaust from an engine has 5 ppm NOx and 10% oxygen concentration, an adjustment of the oxygen concentration to 15% and the NOx level to 7.5 ppm is necessary. Thus, as used herein, the "San Joaquin Air Board Level" takes into account this adjustment in NOx level relative to oxygen concentration such that the oxygen level in the exhaust equals 15%.

In some embodiments, provided herein are systems, methods and devices comprising a reactor that is operatively connected to (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit and exhaust from the reactor contains a San Joaquin Air Board Level equal to or less than about 0.4 grams of NOx per horsepower-hour of electrical energy produced by the engine.

In further or additional embodiments, the exhaust from the reactor contains a San Joaquin Air Board Level equal to or less than about 0.35 grams of NOx per horsepower-hour of electrical energy produced by the engine, or the exhaust from the reactor contains a San Joaquin Air Board Level equal to or less than about 0.3 grams of NOx per horsepower-hour of electrical energy produced by the engine, or the exhaust from the reactor contains a San Joaquin Air Board Level equal to or less than about 0.25 grams of NOx per horsepower-hour of electrical energy produced by the engine, or the exhaust from the reactor contains a San Joaquin Air Board Level equal to or less than about 0.2 grams of NOx per horsepower-hour of electrical energy produced by the engine, or the exhaust from the reactor contains a San Joaquin Air Board Level equal to or less than about 0.15 grams of NOx per horsepower-hour of electrical energy produced by the engine, or the exhaust from the reactor contains a San Joaquin Air Board Level equal to or less than about 0.1 grams of NOx per horsepower-hour of electrical energy produced by the engine, or the exhaust from the reactor contains a San Joaquin Air Board Level equal to or less than about 0.05 grams of NOx per horsepower-hour of electrical energy produced by the engine, or the exhaust from the reactor contains a San Joaquin Air Board Level equal to or less than about 0.03 grams of NOx per horsepower-hour of electrical energy produced by the engine, or the exhaust from the reactor contains a San Joaquin Air Board Level equal to or less than about 0.01 grams of NOx per horsepower-hour of electrical energy produced by the engine.

In some embodiments, provided herein are systems, methods and devices comprising a reactor that is operatively connected to (a) a biogas production unit for converting waste to a biogas stream; and (b) an engine that utilizes the biogas stream from the biogas producing unit to produce energy and an engine exhaust; wherein the reactor decreases NOx emissions from the engine exhaust by contacting the engine exhaust with a liquid waste stream provided from the biogas production unit. In some embodiments, a NOx level in engine exhaust is reduced to a greater extent when contacted with a liquid waste stream than when contacted with tap water (when measured at the same pressure, temperature, pH, and retention time). See Example 4. Unless noted or if context requires otherwise, when comparing the NOx levels between engine exhaust treated with waste water and the NOx levels in engine exhaust treated with tap water as described herein, variables such as initial NOx levels, concentration, pressure, temperature, and retention time are held constant.

It has been determined that in certain embodiments of the subject matter described herein, a significant reduction in NOx level is obtained by treating engine exhaust with waste water when compared to resulting NOx levels from the treatment of engine exhaust (of the same source) with tap water irrespective of pressure. See FIG. 2. In some embodiments, contacting an engine exhaust with waste water provides a NOx level that is at least about 1.1 to about 2.5 times lower than the NOx level obtained from contacting the engine exhaust with tap water. In further or additional embodiments, contacting an engine exhaust with waste water provides a NOx level that is at least about 1.3 to about 2.3 times lower than the NOx level obtained from contacting the engine exhaust with tap water. In further or additional embodiments, contacting an engine exhaust with waste water provides a NOx level that is at least about 1.5 to about 2.1 times lower than the NOx level obtained from contacting the engine exhaust with tap water. In still further or additional embodiments, contacting an engine exhaust with waste water provides a NOx level that is at least about 1.6 to about 2.0 times lower than the NOx level obtained from contacting the engine exhaust with tap water. In some embodiments, contacting an engine exhaust with waste water provides a NOx level that is at least about 1.7 to about 1.9 times lower than the NOx level obtained from contacting the engine exhaust with tap water. In some embodiments, contacting an engine exhaust with waste water provides a NOx level that is at least about 1.8 to about 1.9 times lower than the NOx level obtained from contacting the engine exhaust with tap water.

In further or additional embodiments, contacting an engine exhaust with waste water provides a NOx level that is at least about 1.1 times lower than the NOx level obtained from contacting the engine exhaust with tap water. In further or additional embodiments, contacting an engine exhaust with waste water provides a NOx level that is at least about 1.3 times lower than the NOx level obtained from contacting the engine exhaust with tap water. In further or additional embodiments, contacting engine exhaust with waste water provides a NOx level that is at least about 1.5 times lower than the NOx level obtained from contacting engine exhaust with tap water. In further or additional embodiments, contacting engine exhaust with waste water provides a NOx level that is at least about 1.7 times lower than the NOx level obtained from contacting engine exhaust with tap water. In some embodiments, contacting engine exhaust with waste water provides a NOx level that is at least about 1.9 times lower than the NOx level obtained from contacting engine exhaust with tap water. In still further or embodiments, engine exhaust that has been contacted with waste water provides a NOx level that is at least about 2.0 times lower than the NOx level obtained from contacting engine exhaust with tap water. In still further or embodiments, engine exhaust that has been contacted with waste water provides a NOx level that is at least about 2.1 times lower than the NOx level obtained from contacting engine exhaust with tap water. In still further or embodiments, engine exhaust that has been contacted with waste water provides a NOx level that is at least about 2.2 times lower than the NOx level obtained from contacting engine exhaust with tap water.

Reduction in SOx Emissions

In some embodiments, provided herein are systems, methods and devices comprising a reactor that is operatively connected to (a) a biogas production unit for converting waste to a biogas stream; and (b) an engine that utilizes the biogas stream from the biogas producing unit to produce energy and an engine exhaust; wherein the reactor decreases SOx emissions from the engine exhaust by contacting the engine exhaust with a liquid waste stream provided from the biogas production unit. In some embodiments, a SOx level in engine exhaust is reduced to a greater extent when contacted with a liquid waste stream than when contacted with tap water (when measured at the same pressure, temperature, pH, and retention time). See Example 5. It is understood that, unless noted or if context requires otherwise, when comparing the SOx levels between engine exhaust treated with waste water and the SOx levels in engine exhaust treated with tap water as described herein, variables such as initial SOx levels, concentration, pressure, temperature, and retention time are held constant.

It has been determined that in certain embodiments of the subject matter described herein, a significant reduction in SOx level is obtained by treating engine exhaust with waste water at 15 psi when compared to resulting SOx levels from the treatment of engine exhaust (of the same source) with tap water at 15 psi. See FIG. 3. In some embodiments, contacting an engine exhaust at 15 psi with waste water provides a SOx level that is at least about 2 to about 20 times lower than the SOx level obtained from contacting the engine exhaust at 15 psi with tap water. In further or additional embodiments, contacting an engine exhaust at 15 psi with waste water provides a SOx level that is at least about 4 to about 18 times lower than the SOx level obtained from contacting the engine exhaust at 15 psi with tap water. In some embodiments, contacting an engine exhaust at 15 psi with waste water provides a SOx level that is at least about 6 to about 16 times lower than the SOx level obtained from contacting the engine exhaust at 15 psi with tap water. In further or additional embodiments, contacting an engine exhaust at 15 psi with waste water provides a SOx level that is at least about 7 to about 14 times lower than the SOx level obtained from contacting the engine exhaust at 15 psi with tap water. In some embodiments, contacting an engine exhaust at 15 psi with waste water provides a SOx level that is at least about 8 to about 12 times lower than the SOx level obtained from contacting the engine exhaust at 15 psi with tap water.

In further or additional embodiments, contacting an engine exhaust at 15 psi with waste water provides a SOx level that is at least about 2 times lower than the SOx level obtained from contacting the engine exhaust at 15 psi with tap water. In further or additional embodiments, contacting an engine exhaust at 15 psi with waste water provides a SOx level that is at least about 4 times lower than the SOx level obtained from contacting the engine exhaust at 15 psi with tap water. In some embodiments, contacting engine exhaust at 15 psi with waste water provides a SOx level that is at least about 6 times lower than the SOx level obtained from contacting the engine exhaust at 15 psi with tap water.

In further or additional embodiments, contacting an engine exhaust at 15 psi with waste water provides a SOx level that is at least about 8 times lower than the SOx level obtained from contacting the engine exhaust at 15 psi with tap water. In some embodiments, contacting engine exhaust at 15 psi with waste water provides a SOx level that is at least about 10 times lower than the SOx level obtained from contacting the engine exhaust at 15 psi with tap water. In further or additional embodiments, contacting engine exhaust at 15 psi with waste water provides a SOx level that is at least about 12 times lower than the SOx level obtained from contacting the engine exhaust at 15 psi with tap water. In still further or additional embodiments, contacting engine exhaust at 15 psi with waste water provides a SOx level that is at least about 14 times lower than the SOx level obtained from contacting the engine exhaust at 15 psi with tap water. In certain embodiments, contacting engine exhaust at 15 psi with waste water provides a SOx level that is at least about 16 times lower than the SOx level obtained from contacting the engine exhaust at 15 psi with tap water. In some embodiments, contacting engine exhaust at 15 psi with waste water provides a SOx level that is at least about 18 times lower than the SOx level obtained from contacting the engine exhaust at 15 psi with tap water. In yet further or additional embodiments, contacting engine exhaust at 15 psi with waste water provides a SOx level that is at least about 20 times lower than the SOx level obtained from contacting the engine exhaust at 15 psi with tap water.

Extended Reduction of NOx and SOx

It has been determined that a significant reduction in NOx and SOx is obtained after treatment with a liquid waste stream. See FIG. 5. In embodiments described herein where certain percentages of reduction in NOx, SOx, and or COx levels are provided, these percentages apply to values of NOx, SOx, and or COx corrected to 15% $O_2$ content, and in further or additional embodiments, these percentage apply to situations where the percentages are not corrected to 15% $O_2$ content. In some embodiments, provided herein is a method, device, and system that comprises at least about a 95% reduction in NOx or SOx at a time between about 30 minutes to about 20 hours of treatment levels wherein the percentage of NOx or SOx is corrected to 15% $O_2$ content, and, in further embodiments, the percentage of NOx or SOx is not corrected to 15% $O_2$ content. In further or additional embodiments, at least about a 95% reduction in NOx or SOx level is obtained at a time between about 1 hour to about 15 hours of treatment wherein the percentage of NOx or SOx is corrected to 15% $O_2$ content, and, in further embodiments, the percentage of NOx or SOx is not corrected to 15% $O_2$ content. In yet further or additional embodiments, at least about a 95% reduction in NOx or SOx level is obtained at a time between about 2 hours to about 12 hours of treatment wherein the percentage of NOx or SOx is corrected to 15% $O_2$ content, and, in further embodiments, the percentage of NOx or SOx is not corrected to 15% $O_2$ content. In some embodiments, at least about a 95% reduction in NOx or SOx level is obtained at a time between about 3 hours to about 10 hours of treatment wherein the percentage of NOx or SOx is corrected to 15% $O_2$ content, and, in further embodiments, the percentage of NOx or SOx is not corrected to 15% $O_2$ content. In some embodiments, at least about a 95% reduction in NOx or SOx level is obtained at a time between about 4 hours to about 8 hours of treatment wherein the percentage of NOx or SOx is corrected to 15% $O_2$ content, and, in further embodiments, the percentage of NOx or SOx is not corrected to 15% $O_2$ content. In some embodiments, at least about a 95% reduction in NOx or SOx level is obtained at a time between about 6 hours to about 7 hours of treatment wherein the percentage of NOx or SOx is corrected to 15% $O_2$ content, and, in further embodiments, the percentage of NOx or SOx is not corrected to 15% $O_2$ content. In still further embodiments, at least about a 95% reduction in NOx or SOx level is obtained at a time between about 2 hours to about 5 hours of treatment wherein the percentage of NOx or SOx is corrected to 15% $O_2$ content, and, in further embodiments, the percentage of NOx or SOx is not corrected to 15% $O_2$ content. In yet further or additional embodiments, at least about a 95% reduction in NOx or SOx level is obtained at a time between about 2 hours to about 3 hours of treatment wherein the percentage of NOx or SOx is corrected to 15% $O_2$ content, and, in further embodiments, the percentage of NOx or SOx is not corrected to 15% $O_2$ content.

It has also been determined that NOx and SOx from engine exhaust is substantially reduced (90% or greater) after about 20 hours of treatment with a liquid waste stream wherein the percentage of NOx or SOx is corrected to 15% $O_2$ content, and, in further embodiments, the percentage of NOx or SOx is not corrected to 15% $O_2$ content. See Example 6 (Table 1). In some embodiments, provided herein is a method, device, and system that comprises at least about a 90% to about a 100% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content. In further or additional embodiments, provided herein is a method, device, and system that comprises at least about a 91% to about a 99% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content. In further or additional embodiments, provided herein is a method, device, and system that comprises at least about a 92% to about a 98% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content. In some embodiments, provided herein is a method, device, and system that comprises at least about a 93% to about a 97% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content. In further or additional embodiments, provided herein is a method, device, and system that comprises at least about a 94% to about a 96% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content. In further or additional embodiments, provided herein is a method, device, and system that comprises at least about a 95% reduction in NOx and/or SOx level after about 20 hours of treatment with a liquid waste stream wherein the percentage of NOx or SOx is corrected to 15% $O_2$ content, and, in further embodiments, the percentage of NOx or SOx is not corrected to 15% $O_2$ content.

Engines

Another feature of the subject matter provided herein is an engine that utilizes a biogas stream from a biogas producing unit to produce energy and an engine exhaust; wherein a reactor decreases NOx emissions from the engine exhaust by contacting the engine exhaust with a liquid waste stream provided from the biogas production unit. In some embodiments, the engine is an internal combustion engine, cogeneration unit, or turbine. In further or additional embodiments, the internal combustion comprises at least one biogas engine. In some embodiments, provided are at least two biogas engines. In some embodiments, the engine is a cogeneration unit or turbine.

Biogas engines are commercially available from the following sources: Acterra Group, Inc.; Advanced Green Energy Solutions LLC; Capstone Turbine Corporation; Caterpillar Electric Power; Charles Equipment Company; Cummins Engines; Dresser Waukesha; Guascor; PRO2; FABCO Power Systems; GE Jenbacher Gas Engines; Gen-Tec LLC; Ingersoll Rand Energy Systems; Inland Power Group; Kraft Power Corporation; MAN Engines & Components Inc.; Martin Machinery; Stewart Engineered Equipment Company, Inc.; and Unison Solutions, Inc.

Injection of Fluid into Engine Exhaust

Figure 1:
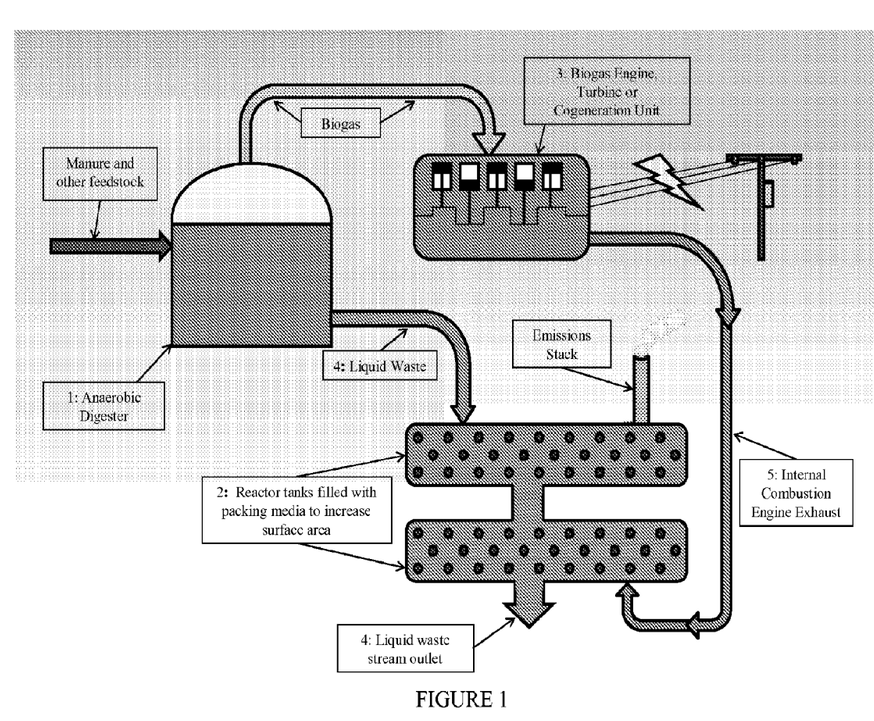
FIG. 1 is a schematic illustration of one non-limiting embodiments of the methods, devices and systems provided herein demonstrating NOx removal for biogas engines placed at an anaerobic digestion facility placed at a concentrated animal feeding operation such as a dairy farm or other waste processing facility such as a waste water treatment plant. The anaerobic digester (1) is provided. In some embodiments, provided is reactor tank (2) attached to an anaerobic digester (1) and engine (e.g., a cogeneration unit, internal combustion engine, or biogas engine (3)). The reactor (2) utilizes urea and other endogenous reducing agents or reactive chemical agents of the liquid waste stream (4) to decrease NOx emissions from the cogeneration unit (3).

Another feature of the subject matter described herein is a method, device and system comprising an engine that is operatively connected to a reactor and the operable connection between the engine and the reactor contains an injection inlet for the introduction of a reactive chemical agent to contact the engine exhaust prior to entrance of the engine exhaust into the reactor. In further or additional embodiments, the reactive chemical agent comprises urea, ammonia, water, or air. For example, in certain embodiments, the injection of fluid is a pretreatment of the engine exhaust and the injection site is at the operable connection between the engine and the reactor (5) of FIG. 1. In some embodiments, the reactive chemical agent comprises urea, ammonia, water, or air. In a specific embodiment, provided is a method comprising the step of decreasing NOx emissions in a reactor that is operatively connected to (a) a biogas production unit for converting waste to a biogas stream; and (b) an engine that utilizes the biogas stream from the biogas producing unit to produce energy and an engine exhaust; wherein the engine exhaust is operatively connected to the reactor and the operable connection between the engine exhaust and the reactor contains an injection inlet for the introduction of a reactive chemical agent to contact the engine exhaust prior to entrance of the engine exhaust into the reactor.

Reactors

Yet another feature of the subject matter provided herein is a method, device and system comprising a reactor that is operatively connected to (a) a biogas production unit for converting waste to a biogas stream; and (b) an engine that utilizes the biogas stream from the biogas producing unit to produce energy and an engine exhaust. The reactor of the methods, devices and systems provided herein facilitates the attenuation of NOx emission from biogas combustion utilizing a liquid waste stream utilizing principles of extended absorption, wet chemical scrubbing, and/or selective non-catalytic reduction. In certain embodiments, the reactor comprises packing media to increase the surface area for the removal of NOx, COx, and SOx from engine exhaust.

Agents Used in the Reactor

Provided herein, in certain embodiments, is a reactor comprising at least one reactive chemical agent that is provided from a liquid waste stream from a biogas production unit. The reactive chemical agent is utilized to decrease the levels of NOx, COx, and/or SOx from engine exhaust. In certain embodiments, the reactive chemical agent is a nitrogen-containing compound. For example, in some embodiments, the nitrogen-containing compound is urea or ammonia. In further or additional embodiments, the reactive chemical agent comprises an oxidizing or reducing agent.

In some embodiments, the reactive chemical agent comprises a reducing agent. In certain embodiments, the reducing agent comprises urea or ammonia. In further or additional embodiments, the reactive chemical agent comprises an oxidizing agent. In some embodiments, the oxidizing agent is oxygen. For example, in certain embodiments, the oxygen is provided from an engine or is exogenous and is provided from a source outside of the system (e.g. air). In further embodiments, the reactive chemical agent comprises urea, ammonia, water, or air. In additional embodiments, at least one reactive chemical agent is provided from a biogas production unit. In yet further embodiments, all of the reactive chemical agents are provided from the biogas production unit. Further, in certain situations, heat from the cogeneration unit (or biogas engine or turbine) is used to augment and/or enhance the chemical reactions occurring in the reactor.

In still further embodiments, the reactive chemical agent comprises a nitrogen-containing compound or a salt thereof. For example, in specific embodiments, the reactive chemical agent comprises isocyanuric acid, a hydroxyl amine, hydrazine, or cyanuric acid. In further or additional embodiments, the reactive chemical agent comprises an ammonium salt. In specific embodiments, the ammonium salt is ammonium carbamate, ammonium carbonate, ammonium bicarbonate, ammonium formate, ammonium acetate, ammonium malate, or ammonium maleate.

Extended Absorption

In a specific embodiment of the subject matter described herein, provided is a method, device and system utilizing a reactor that decreases NOx levels using extended absorption. The process of extended absorption to decrease NOx levels of engine exhaust as utilized in the present disclosure proceeds as follows. The biogas engine burns the biogas to produce an exhaust comprising COx, NOx, and/or SOx.

Hot nitric oxide (NO) is then cooled to approximately 100° F. (38° C.) where it reacts non-catalytically and exothermically with oxygen to form nitrogen dioxide (Equation 1). The cooler temperatures are necessary to prevent the reverse reaction and ensure maximum production of $NO_2$. The final step for producing nitric acid involves absorption of $NO_2$ into water where it reacts to form nitric acid.

The rate of this final reaction is controlled by three important steps: (1) the non-catalytic, gas phase oxidation of NO to $NO_2$, (2) diffusion of the $NO_2$ from the gas phase into the liquid phase, and (3) exothermic chemical reaction with water in the liquid phase (Equation 2). This final step regenerates an equivalent of NO which must either be oxidized to $NO_2$ and absorbed into water or emitted from the system as waste. If not captured within the absorption tower, NOx exits the plant as part of the absorber tail gas emissions. In certain embodiments, NOx is a valuable product as it is readily converted to a desired commercial chemical, nitric acid.

As shown in Equation 3 one mole of NO is formed for every three moles of $NO_2$ absorbed:

$$2NO + O_2 \rightarrow 2NO_2 + \text{heat} \qquad \text{Equation 1}$$

$$3NO_2 + H_2O \rightarrow 2HNO_3 + NO + \text{heat} \qquad \text{Equation 2}$$

Vent gas containing NOx is released to the atmosphere from the reactor only after the gas becomes too dilute to recycle further. Thus, the process of extended absorption as implemented in the present disclosure is utilized in the reactor to remove NOx from the biogas exhaust. In some embodiments, provided is a reactor comprising an absorption chamber that reduces NOx emissions from the engine exhaust using extended absorption.

Yet another feature of the subject matter provided herein is the optimization of an extended absorption process. The four most important factors influencing the efficiency of the extended absorption process provided herein is: (1) temperature, (2) pressure within the absorption chamber (e.g., the reactor), (3) acidity of the absorbing solution, and (4) retention time within the absorption chamber (e.g., reactor).

First, temperature is a parameter in NOx absorption efficiency. Excess heat comes into the system from two sources: the high ambient temperature of the emissions stream and the absorption and subsequent chemical reaction of NOx in the absorbing liquid to form nitric acid. Both the absorption and the reaction are exothermic and release approximately 135 kJ/mole[2]. In some embodiments, provided is a reactor wherein the average temperature within the reactor is within the range of about 50° C. to about 0° C. Without being limited by theory, it is believed that temperature ranges within about 50° C. to about 0° C. will provide optimum conditions for extended absorption resulting in more efficient transfer of NOx from the gas to solution phase. In further or additional embodiments, the average temperature within the reactor is equal to or less than about 50° C., is equal to or less than about 45° C., is equal to or less than about 38° C., is equal to or less than about 35° C., is equal to or less than about 30° C., is equal to or less than about 25° C., is equal to or less than about 20° C., or is equal to or less than about 10° C.

Second, pressure within the absorption chamber is a parameter in NOx absorption efficiency. Without being limited by theory, it is believed that the rate of oxidation of NO and the rate of absorption of $NO_2$ into solution is impacted by pressure because the uncatalyzed air oxidation of NO typically requires minutes, whereas absorption of $NO_2$ is complete within seconds. Thus the oxidation of NO is rate limiting, so additional absorption tower pressure, which in certain embodiments is in the form of compressed air, has its largest impact on overall absorption efficiency through increasing the rate of NO oxidation. In some embodiments, the average pressure within the absorption chamber is maintained in the range of about 1 atm to about 15 atm. In further or additional embodiments, the average pressure within the absorption chamber is within about 4 atm to about 12 atm, or is within about 10 atm to about 6 atm, or is about 8 atm.

Third, acidity of the absorbing solution is a parameter in NOx absorption efficiency. Without being limited by theory, it is believed that more basic conditions are preferred in order to facilitate the dissolution of acidic NOx into solution. In some embodiments, the average pH of the absorbing solution within the reactor is within the range of about 5.5 to about 9. In further or additional embodiments, the pH of the absorbing solution within the reactor is within the range of about 6 to about 8.5, or within about 6.5 to about 8, or is about 7, or is about 8, or is about 8.5, or is about 9, or is about 9.5.

Fourth, retention time within the absorption chamber is a parameter in NOx absorption efficiency. "Retention time" is the period of time a gas sample is maintained in the reactor. Without being limited by theory, it is believed that a longer retention time will result in an increase in the transfer of NOx from the gas to solution phase. Retention time is measured in minutes by dividing the volume of the reactor (in liters) by the flow of gaseous NOx (in liters/minute). In some embodiments, provided is a reactor that has a retention time of NOx within the range of at least about 1 second to at least about 15 seconds. In some embodiments, the retention time is at least about 1 second, at least about 2 seconds, at least about 3 seconds, at least about 4 seconds, at least about 5 seconds, at least about 6 seconds, at least about 7 seconds, at least about 8 seconds, at least about 10 seconds, at least about 12 seconds, at least about 15 seconds, or at least about 20 seconds.

Wet Chemical Scrubbing

In a specific embodiment of the subject matter described herein, provided are methods, devices and systems utilizing a reactor that decreases NOx levels using wet chemical scrubbing. Provided herein are two techniques utilizing acid-base chemistry to decrease NOx emissions from an engine. The processes described herein use either ammonia or urea to "scrub" NOx from engine tail gas streams through conversion to either nitrates or nitrites.

Ammonia-Based Scrubbing

In one embodiment, the reactor utilizes ammonia from a liquid waste stream provided from a biogas production unit to scrub and therefore decrease NOx emissions from an engine. The process proceeds in the following manner to produce ammonium nitrate (Equation 3).

$$NOx + H_2O \rightarrow HNO_3$$

$$HNO_3 + NH_3 \rightarrow NH_4NO_3 \text{(ammonium nitrate)} \quad \text{Equation 3}$$

In certain situations, ammonium nitrite is formed then oxidized to ammonium nitrate. For example, a combination of high dilution and air/photo-oxidation provides the necessary oxidization conditions, as dilute aqueous solutions of ammonium nitrite are oxidized to ammonium nitrate within about 24 hours at room temperature (Equation 4).

$$NO + NH_3 \rightarrow HNO_2$$

$$HNO_2 + NH_3 \rightarrow NH_4NO_2 \text{(ammonium nitrite)}$$

$$NH_4NO_2 + O_2 \rightarrow NH_4NO_3 \quad \text{Equation 4}$$

Urea-Based Scrubbing

In one embodiment, the reactor utilizes urea $((H_2N)_2CO)$ from a liquid waste stream provided from a biogas production unit to scrub and therefore decrease NOx emissions from an engine. This method involves selective non-catalytic reduction (SNCR) of NOx as depicted in the reactions of Equation 5.

$$HNO_2 + (H_2N)_2CO \rightarrow HNCO + N_2 + H_2O$$

$$HNCO + HNO_2 \rightarrow N_2 + CO_2 + H_2O$$

$$HNCO + H_2O \rightarrow NH_3 + CO_2$$

$$HNO_3 + NH_3 \rightarrow NH_4NO_3 \quad \text{Equation 5}$$

In further or additional embodiments, urea can also facilitate the SNCR of nitric acid through the mechanism depicted in Equation 6.

$$6HNO_3 + 5(H_2N)_2CO \rightarrow 8N_2 + 5CO_2 + 13H_2O \quad \text{Equation 6}$$

In still further or additional embodiments, dissolved ammonia, in the form of ammonium hydroxide, within the liquid waste stream participates in SNCR of both nitric and nitrous acid as shown in Equation 7. As shown below, three moles of nitric acid are reduced by five moles of ammonium hydroxide, whereas only one mole of ammonium hydroxide is required to reduce one mole of nitrous acid.

$$3HNO_3 + 5NH_4OH \rightarrow 4N_2 + 14H_2O$$

$$HNO_2 + NH_4OH \rightarrow N_2 + H_2O \quad \text{Equation 7}$$

While certain embodiments have been described, these embodiments have been presented by way of example only, and are not intended to limit the scope of the disclosure. The methods, devices, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

EXAMPLES

The following specific examples are to be construed as merely illustrative, and not limitative of the remainder of the disclosure in any way whatsoever.

In the following examples, the NOx and/or SOx emissions are analyzed at points before and after scrubbing. The measurement of NOx is determined using a portable combustion gas analyzer. Suitable instruments are available through Clean Air Equipment Rental. These instruments (i.e., Model ECOM AC+ or Testo 350XL) can measure $O_2$, CO, $CO_2$, NO, $NO_2$, and $SO_2$ with 2% accuracy over a range from several thousand ppm down to less than 10 ppm. They are designed for either high (up to 1600° F.) or low (30° F.) temperature use in the measurement of boiler flue gas, engine emissions, and the environmental reporting of stack gas parameters.

NOx will be generated by a small internal combustion engine and piped directly into the bottom of the absorption tower. The amount of NOx leaving the engine within the exhaust stream is measured and recorded at the beginning and end of each experiment. Both the length and configuration of the pipe leading to the absorption tower are used to cool the emissions to below 100° F. The exhaust is allowed to fill the absorption tower and exit the top via a stack. Measurements of NOx concentration is obtained and recorded on these emissions as they exit the stack.

Representative liquid waste for use in experimentation will be obtained from the Bull Frog Dairy (El Centro, Calif.). Other suitable sources of liquid waste include Van Ommering Dairy (Lakeside, Calif.) and the Fiscalini Cheese Company (Modesto, Calif.). The bulk of the waste will be stored, when not in use, in a sealed vessel under refrigeration. For experiments, liquid waste is circulated from a measured aliquot within a flask or beaker via electric pump to the top of the absorption tower were it will be pumped into the first chamber and allowed to drain by gravity throughout the entire length of the absorption tower. The liquid will exit the bottom of the absorption tower through a valve and is funneled back into either a separate flask or the original holding flask. In this way a determination is made as to the necessity for either "fresh" or re-circulated digester waste as it relates to the degree of NOx removed via the absorption tower.

Example 1

Optimization of the Scrubbing Apparatus Configuration: Temperature and Pressure within the Absorption Tower The temperature within the absorption tower is kept below 38° C. or 100° F. to ensure efficient absorption of NOx. The high ambient temperature of the biogas exhaust emissions stream can be maintained by piping the exhaust to the absorption tower. The optimal distance between the cogeneration unit and the absorption tower is determined by measuring exhaust temperature as a function of distance from the engine.

The heat generated by the absorption of $NO_2$ into water and subsequent reaction with water to yield nitric acid (exothermic, 135 kJ/mole$^2$) is dissipated through the relatively large volume of waste stream water being cycled through the absorption tower. Furthermore the anaerobic digester liquid waste stream will not exceed 100° F. The added cost associated with installation and maintenance of refrigeration equipment should, therefore, be avoided.

Example 2

Optimization of the Scrubbing Apparatus Configuration: pH of the Absorbing Liquid within the Absorption Tower The optimum operating range for anaerobic digestion is pH 6.8 to 8.5. This is well above the range where $NO_2$ absorption begins to slow down (50% $HNO_3$ where the pH is effectively zero). Furthermore, due to the constant flow design of most anaerobic digesters, "fresh" aqueous waste will be cycling through the absorption tower during all periods of operation. Thus the rate of $NO_2$ absorption as a function of water pH should remain constant and high.

Example 3

Optimization of the Scrubbing Apparatus Configuration: Retention Time of the Emissions within the Absorption Tower In order to obtain sufficiently long retention times a number of absorption chambers are combined in series. The number and size of these chambers is determined by the volume of emissions generated per unit time. As a rough approximation, the volume of the emissions should be equal to the volume of biogas burned plus the volume of air mixed into the gas at the time of combustion. The temperature of the emissions will greatly expand the volume of the emissions, so this approximation is only true after the emissions have cooled.

The examples and embodiments described herein are for illustrative purposes only and various modifications or changes are included within the spirit and purview of this application and scope of the appended claims.

Example 4

Reduction of NOx Emissions from Engine Exhaust Using a Liquid Waste Stream

Figure 2:
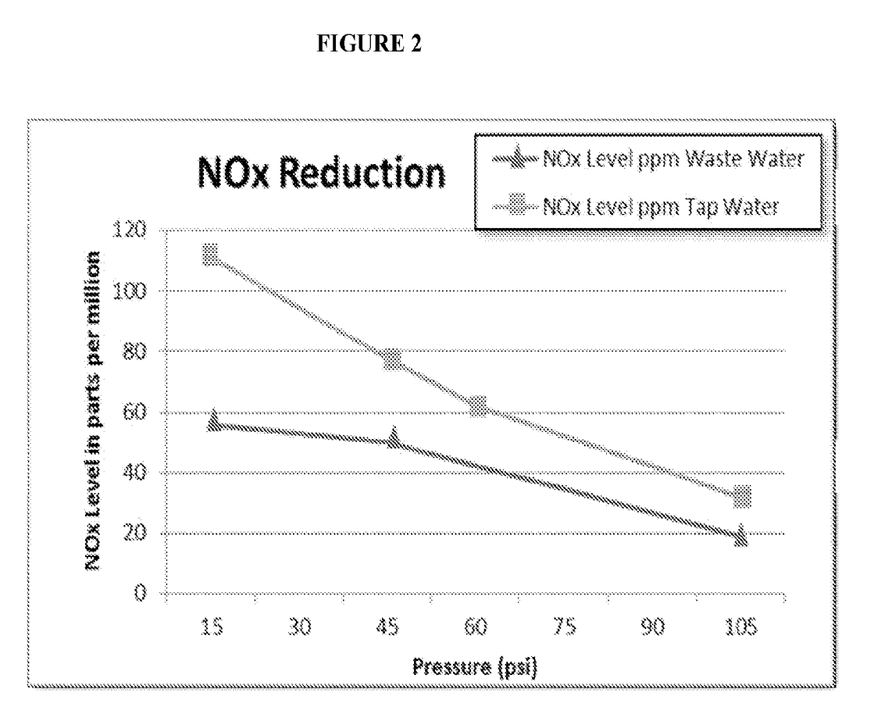
FIG. 2 is a graph showing the reduction of NOx emissions of engine exhaust using a liquid waste stream compared to using tap water. NOx levels (plotted on the y-axis in parts per million (ppm)) at various pressures (plotted on the x-axis in psi) are depicted for both the waste water and tap water samples. See also Example 4.

The level of NOx in an engine exhaust stream from a 2.7 kW diesel powered generator was determined at various scrubber pressures (with temperature, and retention time held constant) before and after contact with: (1) waste water from a dairy-based anaerobic digester (experimental) and (2) tap water (control). The liquid waste for use in experimentation was obtained from the Bull Frog Dairy (El Centro, Calif.). The engine exhaust for each sample was obtained from the same source and passed through a 0.5'×6' scrubbing tower. As shown in FIG. 2, the endogenous compounds present in anaerobic digester waste water effectively remove NOx when contacted with engine exhaust. At all pressures examined (15-105 psi), the waste water showed about a 1.6-fold to about 2-fold improvement over tap water at reducing NOx from engine emissions after passage through a scrubber.

Example 5

Reduction of SOx Emissions from Engine Exhaust Using a Liquid Waste Stream

Figure 3:
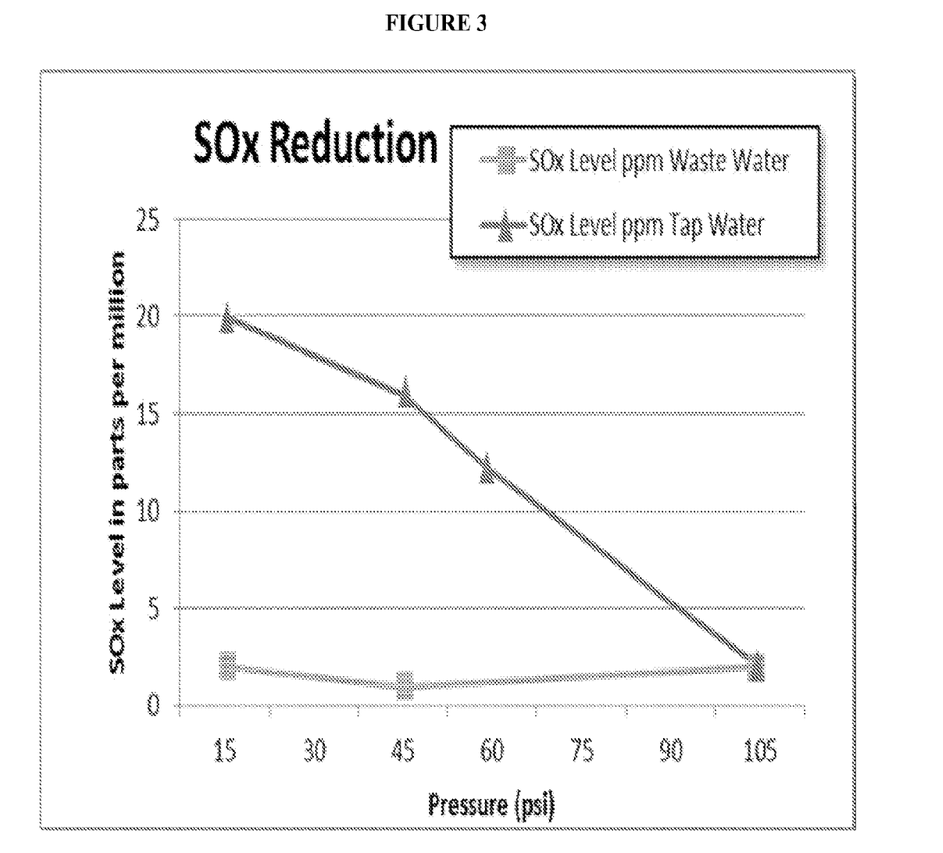
FIG. 3 is a graph showing the reduction of SOx emissions of engine exhaust using a liquid waste stream compared to using tap water. SOx levels (plotted on the y-axis in parts per million (ppm)) at various pressures (plotted on the x-axis in psi) are depicted for both the waste water and tap water samples. See also Example 5.

The level of SOx in an engine exhaust stream from a 2.7 kW diesel powered generator was also determined at various scrubber pressures (with temperature, and retention time held constant) before and after contact with: (1) waste water from a dairy-based anaerobic digester (experimental) and (2) tap water (control). The liquid waste for use in experimentation was obtained from the Bull Frog Dairy (El Centro, Calif.). The engine exhaust for each sample was obtained from the same source and passed through a 0.5'×6' scrubbing tower (as in Example 4). As shown in FIG. 3, at all pressures tested (15-105 psi), the waste water showed nearly complete removal (2 ppm) of SOx from the engine exhaust. For the tap water control, a pressure of 105 psi was required to achieve the 2 ppm SOx level. For example, at 15 psi, the SOx level of tap water-treated engine exhaust was 20 ppm. Thus, at 15 psi, there is about a 10-fold improvement at reducing SOx from the engine emissions using waste water compared to tap water.

Example 6

Figure 4:
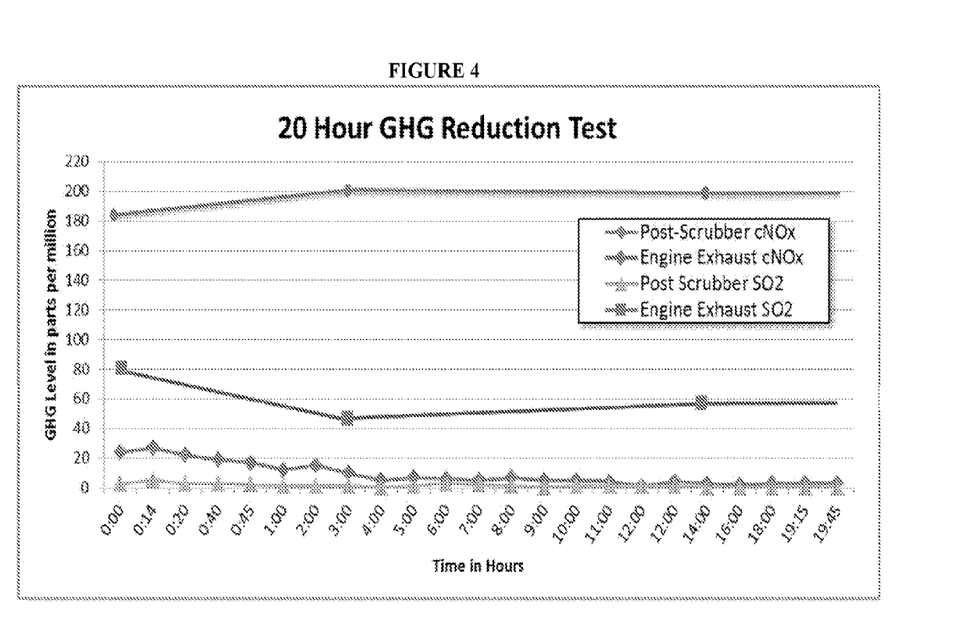
FIG. 4 is a graph showing the significant reduction in green house gases (GHG), including NOx and SOx (in ppm), of engine exhaust when treated with a liquid waste stream over an extended and continuous 20 hour period (comparing pre-treatment "engine exhaust" with "post-scrubber" levels of NOx and SOx). See also Example 6.
Figure 5:
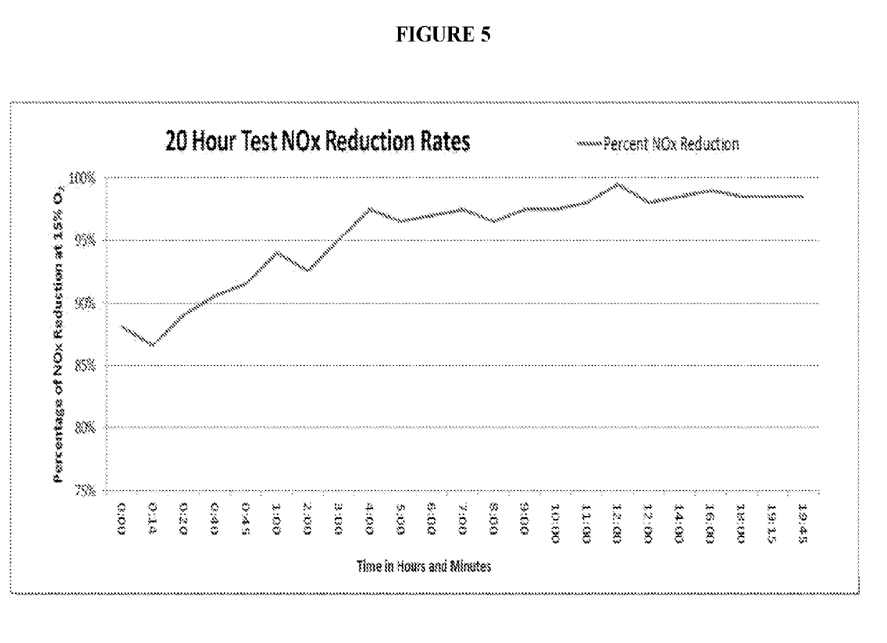
FIG. 5 is a graph showing the significant reduction in NOx (as a percentage of reduction of NOx corrected for an oxygen concentration of 15%) of engine exhaust when treated with a liquid waste stream over an extended and continuous 20 hour period.

Extended 20 Hour Continuously Operated System for Increased Reduction of NOx and SOx from Engine Exhaust Using a Liquid Waste Stream A 2.7 kW diesel powered generator was used as a stationary source of engine exhaust containing NOx and SOx. The engine exhaust was treated with waste water for an extended 20 hour period at 80 psi and passed through the scrubber at approximately 0.5 standard cubic feet per minute. The liquid waste for use in experimentation was obtained from the Bull Frog Dairy (El Centro, Calif.). As shown in FIG. 4, a significant reduction in NOx and SOx was obtained over the course of the 20 hour period of time the engine exhaust was treated with waste water. FIG. 5 presents the percentage of NOx reduction in particular over the 20 hour treatment period corrected for an oxygen concentration of 15%. FIG. 5 shows a greater than about 95% reduction in NOx at about 3 minutes into the experiment after treatment with waste water. Table 1, below, provides the greenhouse gas (GHG) reductions from the 20 hour continuous experiment as percentages over the duration of the experiment. All measured gases (NO, $NO_2$, $SO_2$) were reduced by an average of greater than 94% t after about 20 hours of treatment. The value of cNOx in Table 1 is the total amount of NO and $NO_2$ corrected for an oxygen concentration of 15%.

TABLE 1

| GHG Reduction 20 Hour Test Averages | | | |
| --- | --- | --- | --- |
| GHG | Before (ppm) | After (ppm) | % Reduction |
| NO: | 65.3 | 3.7 | 94.3% |
| $NO_2$: | 64.2 | 0.0 | 100.0% |
| $SO_2$: | 51.3 | 1.3 | 97.5% |
| $cNO_x$: | 202.3 | 9.1 | 95.5% |

What is claimed is:

1. A system comprising: (a) a biogas production unit for converting waste to biogas and liquid waste; and (b) an engine connected to the biogas production unit, the engine configured to: i) receive biogas; and ii) produce energy and an engine exhaust from the biogas; and (c) a reactor comprising: i) an inlet for receiving liquid waste from the biogas production unit; ii) an outlet for liquid waste to exit the reactor; and iii. an absorption chamber that permits flow of the liquid waste from the inlet for receiving liquid waste from the biogas production unit to the outlet for liquid waste to exit the reactor, and wherein NOx emissions in the engine exhaust are decreased by contacting the engine exhaust with liquid waste, thereby producing an emission with at least about 1.1 times less NOx relative to the engine exhaust.

2. The system of claim 1 further provided that the biogas production unit is an anaerobic digester.

3. The system of claim 1 further provided that the biogas production unit is a landfill.

4. The biogas production unit of claim 1 further provided that the waste is biological waste, agricultural waste, or municipal waste.

5. The anaerobic digester of claim 1 further provided that the engine utilizes biogas from the biogas production unit.

6. The system of claim 1 further provided that the emission is produced with at least about 1.1 times less NOx when compared to the NOx level obtained from contacting the engine exhaust with tap water instead of liquid waste.

7. The system of claim 1 wherein the absorption chamber further decreases SOx emissions from the engine exhaust by contacting the engine exhaust with the liquid waste.

8. The system of claim 1 wherein the absorption chamber further decreases COx emissions from the engine exhaust by contacting the engine exhaust with the liquid waste.

9. The system of claim 1 further provided that the engine is operatively connected to the reactor and the operable connection between the engine and the reactor contains an injection inlet for the introduction of a reactive chemical agent to contact the engine exhaust prior to entrance of the engine exhaust into the reactor.

10. The system of claim 1 further provided that the reactor is configured to produce emission with about 1.1 to about 2.5 times less NOx when compared to the NOx level obtained from contacting the engine exhaust with tap water instead of liquid waste.

11. The system of claim 1 further provided that that the reactor is configured to produce emission with at least about 90% less NOx relative to the engine exhaust.

12. A method comprising the step of decreasing NOx emissions using a reactor that is operatively connected to: a. a biogas production unit for converting waste to biogas; and b. an engine connected to the biogas production unit, the engine configured to: i. receive biogas; and ii. produce energy and an engine exhaust from the biogas; further provided that the step comprises decreasing NOx emissions from the engine exhaust by contacting the engine exhaust with liquid waste provided from the biogas production unit in an absorption chamber of the reactor that permits flow of the liquid waste from an inlet to an outlet thereby producing an emission with at least about 1.1 times less NOx relative to the engine exhaust.

13. The method of claim 12 that provides (a) at least about 1.1 times lower NOx level when compared to the NOx level obtained from contacting the engine exhaust with tap water instead of liquid waste or (b) exhaust that contains an amount equal to or less than about 0.75 pounds of NOx per MWh of energy produced by the engine.

14. The method of claim 12 further provided that that the reactor is configured to produce emission with about 1.1 to about 2.5 times less NOx when compared to the NOx level obtained from contacting the engine exhaust with tap water instead of liquid waste.

15. The method of claim 12 further provided that that the reactor is configured to produce emission with at least about 90% less NOx relative to the engine exhaust.

\* \* \* \* \*